United States Patent [19]

Hommeltoft

[11] Patent Number: 5,396,018
[45] Date of Patent: Mar. 7, 1995

[54] METHOD OF RECOVERY ACID CATALYST FROM ACID CATALYZED PROCESSES

[75] Inventor: Sven I. Hommeltoft, Hillerod, Denmark

[73] Assignee: Haldor Topsoe A/S, Lyngby, Denmark

[21] Appl. No.: 142,801

[22] Filed: Oct. 25, 1993

[30] Foreign Application Priority Data

Oct. 27, 1992 [DK] Denmark ............... 1310/92

[51] Int. Cl.⁶ .................................................. C07C 2/62
[52] U.S. Cl. .................................. 585/724; 585/725; 585/726
[58] Field of Search ............... 585/724, 725, 726

[56] References Cited

U.S. PATENT DOCUMENTS 4,209,656  6/1980  Prescott et al.
5,306,859  4/1994  Eastman et al. ............ 585/724

*Primary Examiner*—Asok Pal
*Attorney, Agent, or Firm*—Ostrolenk, Faber, Gerb & Soffen

[57] ABSTRACT

Process for the recovery of acid catalyst from acid catalyzed hydrocarbon conversion processes comprising the steps of: passing a product stream of converted hydrocarbons leaving the hydrocarbon conversion process and containing the acid catalyst through a fixed bed of a solid adsorbent material having affinity for the acid catalyst and, thereby, adsorbing the acid catalyst on the material; desorbing the adsorbed acid catalyst by passing a process stream of hydrocarbons through the adsorbent bed; and cycling the process stream together with the desorbed acid catalyst contained therein to the hydrocarbon conversion process.

14 Claims, No Drawings

METHOD OF RECOVERY ACID CATALYST FROM ACID CATALYZED PROCESSES

BACKGROUND OF THE INVENTION

The present invention concerns acid catalyzed hydrocarbon conversion processes, and, more particular, recovery of valuable acid catalysts from a product stream leaving a hydrocarbon conversion process.

Acid catalyzed processes are most usually employed in the industrial isomerization and hydration of hydrocarbons and during the preparation of high octane gasoline products by alkylation of paraffinic hydrocarbons.

In those processes, a strong acidic compound is conventionally mixed with a hydrocarbon feedstock in a reaction vessel and agitated for a sufficient time until the desired reaction is completed. The final product containing, furthermore, the acid catalyst is then recovered from the reactor effluent by extraction or distillation.

Acid catalysts most usually employed in the above processes are sulphuric acid and hydrogen fluoride. Other acidic compounds suitable as catalysts in hydrocarbon conversion processes are the strong fluorinated sulphuric or sulphonic acids.

Alkylation of paraffins with olefins in the presence of a fluorinated sulphonic acid catalyst supported on polar contact material is mentioned in EP 433,954. The acid catalyst is by the process of EP 433,954 recovered from an alkylate product stream by extraction with water and distillation of the extracted catalyst.

Removal of sulphonic or sulphuric acid catalyst from a reaction mixture by contacting the mixture with hydrotalcite is disclosed by GB 1,570,932. Hydrotalcite is, thereby, added in form of a powder or as particles to the reaction mixture and the mixture agitated until almost all acidic substances from the mixture are transferred into hydrotalcite and removed by reaction with hydrotalcite. After the reaction, hydrotalcite is separated from the mixture by filtration to obtain a neutral solution.

The above reference is completely silent on recovery of acid catalyst after reaction with hydrotalcite.

In many acid catalyzed processes, it is, however, desirable to recover and reuse the recovered acid catalyst in the processes to improve-process economy and diminish environmental risk during storage and final processing of spent catalyst.

It is thus the general object of this invention to provide a method for the recovery of acid catalyst from a product stream leaving acid catalyzed processes, by which method the removed catalyst is recovered and recycled to the process without further processing of the recovered catalyst.

DESCRIPTION OF THE INVENTION

The inventive method for the recovery of acid catalysts from acid catalyzed hydrocarbon conversion process comprises the steps of passing a product stream leaving the conversion process and containing the acid catalyst through a fixed bed of a solid adsorbent material and, thereby, adsorbing the acid catalyst on the material;

recovering the adsorbed acid catalyst by passing a process stream of hydrocarbons through the bed and desorbing the adsorbed acid catalyst into the process stream; and cycling the process stream together with the acid catalyst contained therein back to the conversion process.

By the method of the invention, troublesome treatment by distillation, extraction or filtration in the removal of acid catalyst from a product stream leaving an acid catalyzed process is avoided.

The acid catalyst is continuously removed from the product stream when passing the stream through an adsorption column loaded with the adsorbent and adsorbing the acid catalyst on the adsorbent through polar interaction between the acid and polar groups of the adsorbent. Adsorption takes place at substantially the same process conditions as in the previous conversion process and no detrimental side-reactions proceed in the product stream during removal of the catalyst.

Adsorbed acid catalyst is in a subsequent desorption step recovered by continuously passing a hydrocarbon process stream through the adsorbent. Thereby, desorption is effected by interaction of the adsorbed acid catalyst with reactive compounds such as olefinic and aromatic hydrocarbons present in the process stream.

In practising the above method industrially, convenient adsorption conditions will usually comprise in the temperature interval of between −20° and 50° C. and a pressure of 1 and 20 bar, although higher temperatures and pressures are practicable, particularly in case of hydrogen fluoride catalyst recovery.

Depending on the polarity of the adsorption material and the reactivity of the process stream used during desorption of the acid catalyst, it may be convenient to slightly elevate the temperature and/or reactivity of the process stream during the desorption of the acid catalyst in order to afford desired desorption rates. Increased desorption activity may be achieved by increasing the content of olefins in the process stream.

Suitable adsorption materials comprise any of the non-basic materials with polar surface groups, and with sufficient adsorption capacity to provide high adsorption rates during passage of the acid catalyst containing product stream through the materials.

Preferred adsorption materials include silica, alumina, titania, zirconia and activated carbon for recovery of fluorinated sulphuric and sulphonic acids. In case of hydrogen fluoride catalyst recovery, adsorbent materials preferably comprise metal fluorides including the fluorides of sodium, potassium, lithium, aluminum, magnesium, calcium, zirconium and niobium optionally supported on a carrier of inert material, such as activated carbon. Further preferred hydrogen fluoride adsorbents comprise of HF-salts of basic resins, such as amino resins.

By use of the inventive method substantially cost savings in acid catalyzed hydrocarbon conversion processes are obtained through adsorption and desorption of the catalyst in a single equipment and recycling of desorbed acid back to the conversion process without extensive processing of the catalyst as necessary during catalyst recovery by the known methods. The method is, in particular, useful in hydrogen fluoride catalyzed processes, where the environmental risk during storage and processing of large amounts of this hazardous compound are appreciately diminished.

The above as well as other advantages of the invention will become further evident from the following Examples.

EXAMPLE 1

Recovery of trifluoromethanesulphonic acid catalyst from an alkylated product stream.

A product stream from alkylation of i-butane with 1-butene alkylating agent in the presence of trifluoromethanesulphonic acid catalyst was treated for the recovery of the acid catalyst by adsorption and desorption on a silica adsorbent according to the invention. The product stream leaving the alkylation process contained 30–100 ppm of the acid catalyst and was passed through an adsorption column loaded with 500 ml of the silica adsorbent (Silica Gel 100, particle size 0.2–0.5 mm, as supplied by E. Merck, FRG).

At an inlet temperature of 15° C. and a flow of 7 kg/hour of the product stream through the column, substantially all of the acid catalyst in the product stream was adsorbed on the adsorbent resulting in an effluent stream from the adsorption column with an acid concentration of below 1 ppm. After passage of about 46 kg product stream through the column, the acid concentration in the effluent stream was still below 1 ppm. The concentration of non-adsorbed acid raised to 5 ppm upon passage of 98 kg product stream. After 975 kg product stream have been passed through the column, 20 ppm acid catalyst were found in the effluent stream. The flow of product stream through the column was then stopped. In a subsequent desorption cycle, adsorbed acid was desorbed into an alkylation process stream with 10 vol % 1-butene in i-butane. By passage of 2.8 kg process stream at 40° C. through the column, most of the adsorbed acid was recovered.

EXAMPLE 2

An alkylated product stream similar to that of Example 1 was treated in a 1 liter adsorption column containing 360 g of the above silica adsorbent. 100 adsorption-desorption cycles were carried out. During each adsorption cycle 4 kg/hour product stream containing 35 ppm trifluoromethanesulphonic acid catalyst were passed for 4.5 hours at about 20° C. through the column. The acid content in the purified product stream after the column has in all adsorption cycles been reduced to a concentration of about 2 ppm on an average.

Between each adsorption cycle, the adsorbed acid catalyst was recovered by desorption into an alkylation process stream of 13 vol % 2-butene in i-butane. The stream was passed at 50° C. in the same flow direction as in a foregoing adsorption cycle through the column. After passage of 19.7 kg process stream in the course of 4.5 hours substantially all of the adsorbed acid catalyst has been desorbed and recycled back to the alkylation process.

EXAMPLE 3

Test of amino adsorbents in the recovery of hydrogen fluoride catalyst.

Polystyreneamine (Amberlite IR 45(OH), supplied by BDH Laboratory Reagents) and Polyvinylpyridine (25% crosslinked with divinylbenzene, supplied by Fluka) were tested for their ability reversibly to adsorb hydrogen fluoride.

10 g samples of the above materials were added to a 100 ml beaker and suspended in 30 ml anhydrous hydrogen fluoride (HF) at 10° C. for 5 min. Thereafter, excess of HF was evaporated by warming up the suspension to 20° C.

The amount of HF adsorbed on the materials was subsequently determined by NaOH titration of 1 g portions of the treated samples. After 48 hours at 20° C., the amount of HF adsorbed on polystyreneamine was 0.204 g/g adsorbent and polyvinylpyridine 0.381 g/g adsorbent.

Adsorbed HF was desorbed from the materials by elevating the temperature of the samples. NaOH titration of HF-treated polystyreneamine showed that after 5.5 hours at 50° C. the amount of HF adsorbed on the amine was reduced to 0.197 g/g amine and after 24 hours at 100° C. to 0.0827 g.

Desorption of HF from polyvinylpyridine was effected at 60° C. for 20 hours and at 100° C. for 7.75 hours, showing a decrease of adsorbed HF to 0.220 g/g material to 0.060 g, respectively.

What is claimed is:

1. Process for the recovery of acid catalyst from acid catalyzed hydrocarbon conversion processes comprising the steps of
    passing a product stream of converted hydrocarbons leaving the hydrocarbon conversion process and containing the acid catalyst through a fixed bed of a solid absorbent material having affinity for the acid catalyst and, thereby, adsorbing the acid catalyst on the material;
    desorbing the adsorbed acid catalyst by passing a process stream of hydrocarbons through the adsorbent bed; and
    cycling the process stream together with the desorbed acid catalyst contained therein to the hydrocarbon conversion process;
    wherein the reactivity of the process stream is elevated by increasing the amount of at least one olefinic or aromatic compound in the process stream.

2. The process of claim 1, wherein the acid catalyst comprises a fluorinated sulphonic acid.

3. The process of claim 1, wherein the acid catalyst comprises hydrogen fluoride.

4. The process of claim 2, wherein the adsorbent material comprises silica, alumina, titania, zirconia, activated carbon or mixtures thereof.

5. The process of claim 3, wherein the adsorbent material comprises fluorides of sodium, potassium, lithium, aluminium, magnesium, calcium, zirconium, niobium or HF salts of basic resins.

6. The process of claim 5, wherein the resins comprise HF salts of polystyreneamine or polyvinylpyridine.

7. The process of claim 5, wherein the adsorbent material further comprises a carrier of inert material.

8. The process of claim 1, wherein the adsorbed acid catalyst is desorbed by elevating the temperature of the process stream.

9. The process of claim 1, wherein the process stream comprises a mixture of paraffinic and olefinic hydrocarbons for preparation of high octane gasoline by acid catalyzed alkylation of the paraffinic hydrocarbon with the olefinic hydrocarbons.

10. A catalyzed hydrocarbon conversion process comprising the steps of providing a hydrocarbon alkylation reaction stream comprising the olefin to be alkylated and the alkylation agent, causing the alkylation to be effected in the presence of an acid catalyst, recovering a product stream of alkylated olefin containing acid catalyst, passing the product stream through a fixed bed of solid absorbent material having affinity for the acid catalyst and, thereby, absorbing the acid catalyst on the material, providing a process stream containing a concentration of at least one olefinic or aromatic compound greater than that in the reaction stream, passing the process stream through the absorbent bed thereby desorbing the absorbed acid catalyst, and cycling the process stream together with the desorbed acid catalyst contained therein to the alkylation step.

11. The process of claim 10, wherein the acid catalyst comprises a fluorinated sulphonic acid.

12. The process of claim 10, wherein the acid catalyst comprises hydrogen fluoride.

13. The process of claim 10, wherein the reaction stream comprises a mixture of paraffinic and olefinic hydrocarbons for preparation of high octane gasoline by acid catalyzed alkylation of the paraffinic hydrocarbons with the olefinic hydrocarbons.

14. The process of claim 13, wherein the acid catalyst comprises hydrogen fluoride.

\* \* \* \* \*